United States Patent [19]

Orec et al.

[11] Patent Number: 4,913,140
[45] Date of Patent: Apr. 3, 1990

[54] FLOAT-CONTROLLED HUMIDIFIER

[75] Inventors: Ilija Orec; Erwin J. Meyer, both of Auckland, New Zealand

[73] Assignee: Fisher & Paykel Limited, Auckland, New Zealand

[21] Appl. No.: 233,078

[22] Filed: Aug. 17, 1988

[30] Foreign Application Priority Data

Sep. 7, 1987 [NZ] New Zealand .................. 221689

[51] Int. Cl.[4] ................ A61M 11/04; A61M 15/00
[52] U.S. Cl. ....................... 128/203.16; 128/203.26; 137/451; 261/139
[58] Field of Search ............... 128/203.12, 203.16, 128/203.17, 204.14, 204.17, 200.21, 203.26, 203.27, 200.14; 137/451

[56] References Cited

U.S. PATENT DOCUMENTS

| 513,804 | 1/1894 | Madden | 128/203.16 |
|---|---|---|---|
| 1,269,048 | 6/1918 | Butcher | 137/451 |
| 1,601,258 | 9/1926 | Pajer | 128/203.17 |
| 2,184,679 | 12/1939 | Myrick | 128/203.27 |
| 2,897,554 | 8/1959 | Myrick | 128/203.27 |
| 3,356,460 | 12/1967 | King et al. | 137/451 |
| 3,385,316 | 5/1968 | Couffer, Jr. | 137/451 |
| 3,670,751 | 6/1972 | Buswell | 137/451 |
| 3,996,960 | 12/1976 | Martinez-Lozano | 137/451 |
| 4,051,205 | 9/1977 | Grant | 128/204.14 |
| 4,060,576 | 11/1977 | Grant | 128/203.27 |
| 4,114,642 | 9/1978 | Robbins | 137/451 |
| 4,122,862 | 10/1978 | Brandelli | 137/451 |
| 4,186,764 | 2/1980 | Ottersen et al. | 137/451 |
| 4,201,204 | 5/1980 | Rinne et al. | 128/203.27 |
| 4,352,371 | 10/1982 | Walters | 137/451 |
| 4,431,025 | 2/1984 | Edwards | 137/451 |
| 4,527,584 | 7/1985 | Miller | 137/451 |
| 4,529,002 | 7/1985 | Jacobson | 137/451 |
| 4,676,237 | 6/1987 | Wood et al. | 128/204.14 |
| 4,708,831 | 11/1987 | Elsworth et al. | 128/203.17 |
| 4,753,758 | 6/1988 | Miller | 128/203.27 |

FOREIGN PATENT DOCUMENTS

| 1157348 | 3/1952 | Fed. Rep. of Germany | 128/200.14 |
|---|---|---|---|
| 443874 | 10/1912 | France | 128/203.16 |
| 449781 | 3/1913 | France | 128/203.16 |

Primary Examiner—Edgar S. Burr
Assistant Examiner—Kimberly L. Asher
Attorney, Agent, or Firm—Fleit, Jacobson, Cohn, Price, Holman & Stern

[57] ABSTRACT

A humidifier for humidifying gases flowing from a source to a person, e.g. a patient breathing apparatus, has a gas chamber interconnected with a water compartment and at least one float controlled valve which controls the flow of water into the water compartment so that if the level of water in the gas chamber exceeds a predetermined level, flow of water to the water compartment is prevented. A further float controlled valve may be provided to prevent flow of water from the water compartment to the gas chamber when the water level in the gas chamber exceeds the predetermined, or a further predetermined, level.

11 Claims, 3 Drawing Sheets

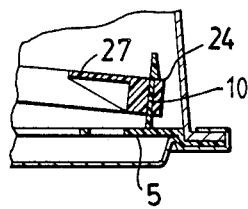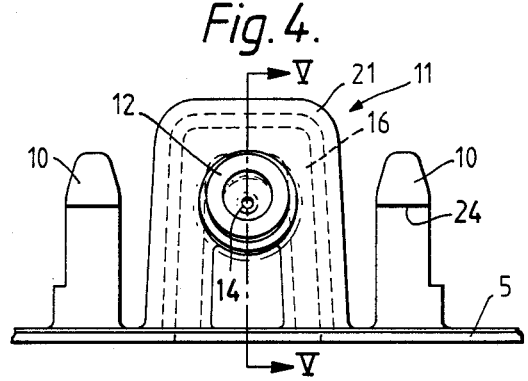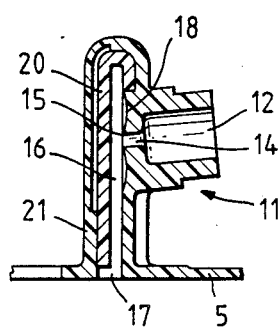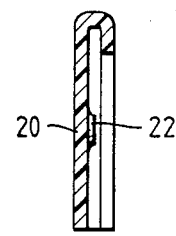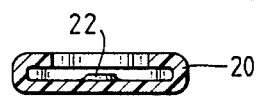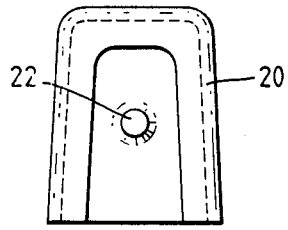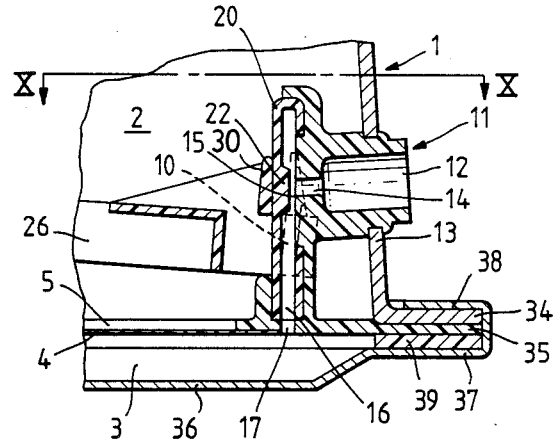

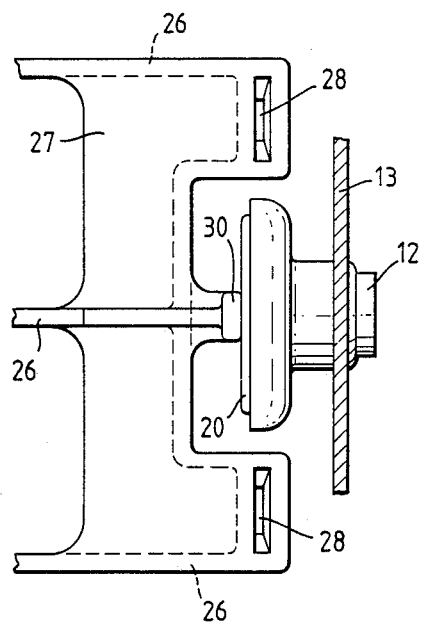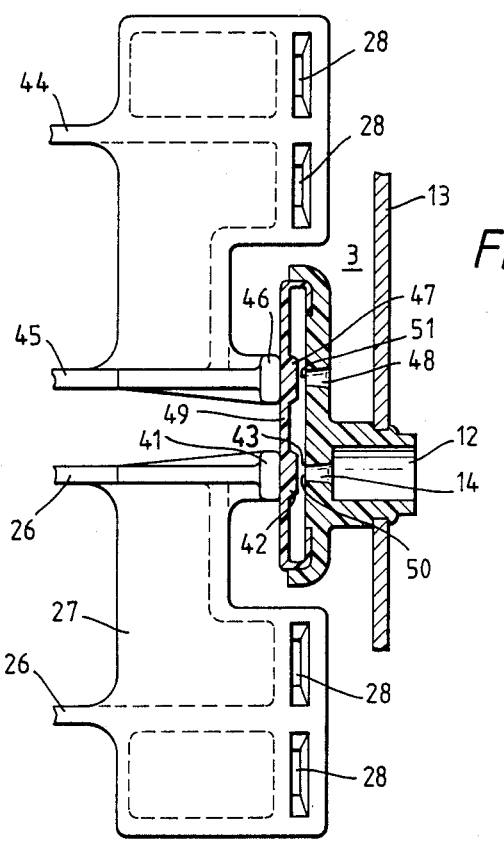

FLOAT-CONTROLLED HUMIDIFIER

BACKGROUND OF THE INVENTION

Field of the Invention

This invention relates to humidifiers and particularly, though not solely, for use in providing humidified gases to a patient in a hospital in need of such humidified gases, for example, in intensive care situations.

BRIEF SUMMARY OF THE INVENTION

It is an object of the invention to provide an apparatus for humidifying gases comprising a gas chamber having an inlet and an outlet to enable gases to be passed through said chamber; an interconnected water compartment; a float in the gas chamber; a water inlet and a water conduit leading to the water compartment; and a water control valve having a movable member and a valve seat in the water conduit, the movable member being movable by the float so that when more than a predetermined amount of water enters the gas chamber from the water compartment, the float actuates the movable member relative to the valve seat to prevent further entry of water into said water compartment.

In a further aspect the invention consists in a conduit for fluid containing a valve constructed, arranged and operable substantially as herein described with reference to and as illustrated by the accompanying drawings.

In a still further aspect the invention consists in a conduit for fluid and containing a valve, the valve comprising a valve seat surrounding a valve orifice leading into the conduit and a flexible wall to the conduit, part of the flexible wall also acting as a movable member of the valve, and valve actuating means operable to apply pressure to the part of the flexible wall which actuating means on the movable member causing closing of the valve and release of pressure permitting flow of fluid through the conduit.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

The invention will now be described in detail with reference to the accompanying drawings wherein:

FIG. 3 is a fragmented cross-sectional view showing a hinging means between a wall mounting means and an arm carrying a float;

FIG. 4 is an enlarged elevational view of a connection means and valve forming part of the invention;

FIG. 5 is a cross-sectional view taken along line V—V of FIG. 4;

FIGS. 6, 7 and 8 are respectively a vertical cross-sectional, a horizontal cross-sectional and an elevational view of a flexible valve member forming part of the valve of FIGS. 4 and 5;

FIG. 9 is an enlarged cross-sectional view of the valve and associated parts of the construction shown in FIG. 1;

FIG. 10 is a cross-sectional view taken along line X—X of FIG. 9 with certain parts omitted; and FIG. 11 is a view similar to FIG. 10 but showing a different embodiment using a double valve arrangement.

DETAILED DESCRIPTION

Figure 1:
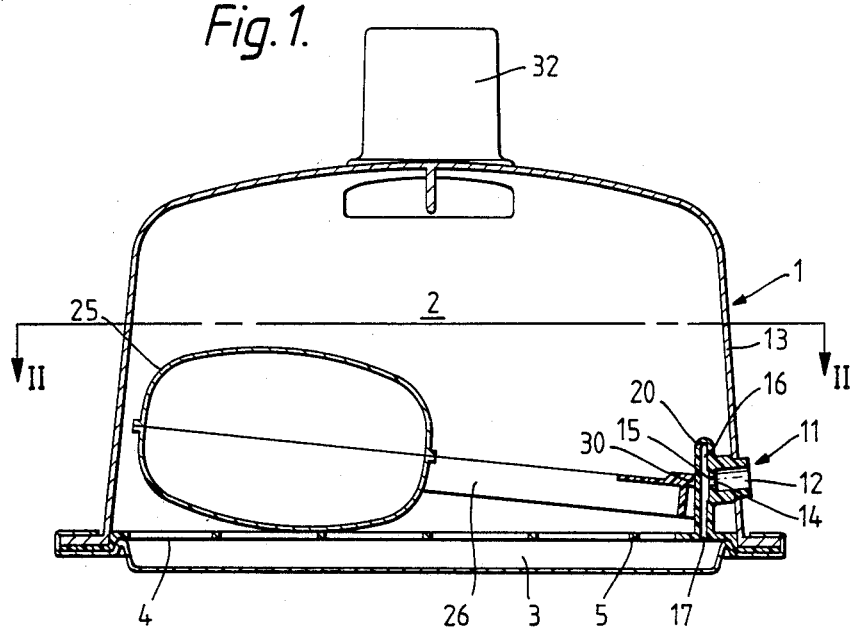
FIG. 1 is a cross-sectional view, taken along line I—I of FIG. 2, of a humidifier constructed according to the invention.

Referring to the drawings, a humidifier 1 is provided with a gas chamber 2 and a water compartment 3, the gas chamber 2 being interconnected with the water compartment 3 by being disposed above the water compartment 3 and a microporous wall 4 between and common to the chamber 2 and the water compartment 3. The microporous wall is made of a microporous material having the property of being permeable to water vapor but substantially impermeable to liquid water and is made for example of expanded PTFE (polytetrafluoroethylene) and the material is preferably flexible, inert and hydrophobic. Such a material is sheet material manufactured under the trade name Gortex and is available from W. L. Gore and Associates Inc., Delaware, U.S.A.

Figure 2:
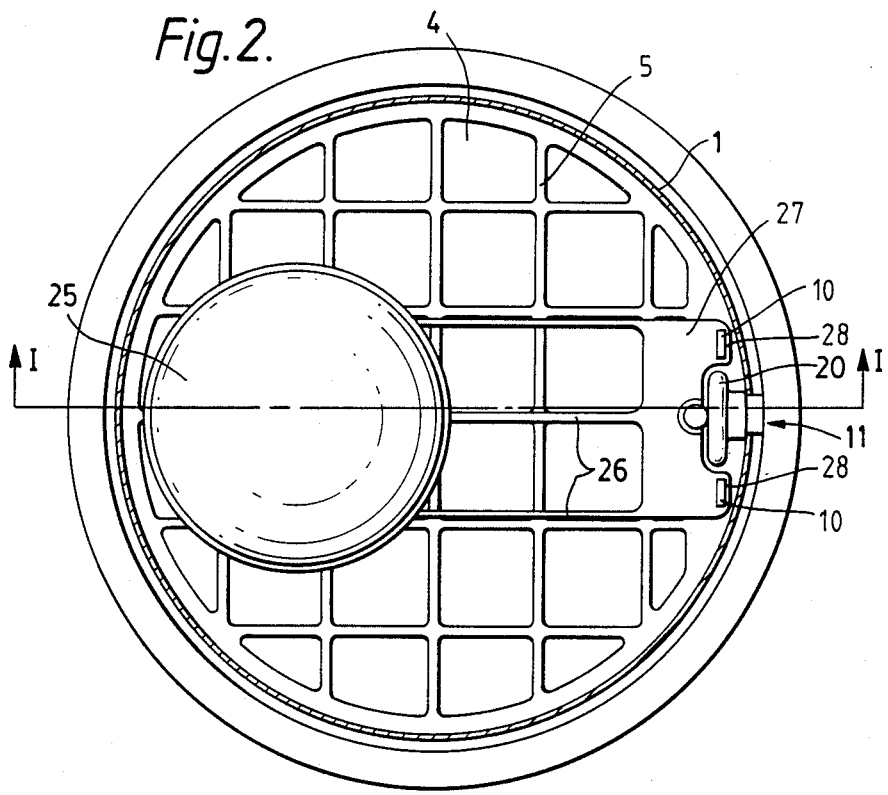
FIG. 2 is a cross-sectional view taken along line II—II of FIG. 1.

This material is thin and to resist the pressures operating due to water being fed to the water compartment 3 from a bag (not shown) suspended on a pole (not shown) positioned adjacent to a hospital patient using the humidifier, the microporous material is mounted on a supporting frame 5 which as may be seen from FIG. 2 is arranged in a horizontal plane with a series of crossing ribs below which the microporous material 4 is positioned. Any suitable rib pattern may be used.

The support 5 is made of a plastics material and molded during an injection molding operation, which at the same time, provides a pair of upstanding strips 10 and a water connection mount 11 molded integrally with the support 5. The water connection mount 11 has a water inlet 12. The mount 11 is mounted in the wall 13 of the gas chamber 2 by using a solvent cement or otherwise as desired. A water delivery orifice 14 is provided in the molded product surrounded by a valve seat 15 leading to a passageway in the form of a slot 16 which passes through the microporous wall support member 5 and thus leads through an outlet 17 into the water compartment 3. A flexible member 20 is molded in a separate operation for example from thin sheet synthetic rubber, e.g. T.P.R. Santoprene 271-47 in a shape as shown in FIGS. 4 to 10 and in the above molding operation to provide the support 5, the flexible member 20 is molded into the outer perimeter 21 of the water connection, the flexible member 20 thereby forming a front wall of the slot 16 and sealing the slot 16 apart from gas chamber 2. The flexible member 20 has a thickened part 22 which provides a valve member which if pressed against the valve seat 15 closes off the entry of water to the slot 16 and thus the water compartment 3.

To assist in giving a complete closing off action the part 18 (FIG. 5) of the water connection close to the valve seat 15 is, if desired, made of a comparatively thick section, shrinkage of which causes an annular protruding lip to be formed about the orifice 14 to form the valve seat 15 as shown in cross section in FIG. 5.

To effect such closing off, a float 25 is provided connected to a set of arms 26, and a cross member 27 is provided with slots 28 (see FIG. 10) which in use slip over the upstanding strips 10. The strips preferably have shoulders 24 near the free ends to prevent inadvertent lifting off of the slotted arms. The slots 28 and strips 10 provide a hinge mechanism, the strips 10 bending when the float 25 moves up for example due to water being present in the gas chamber 2. The cross member 27 carries and actuating member 30 which presses against the flexible member 20 opposite the orifice 14 and thus exerts considerable pressure on the member 20 against the seat 15 due to the leverage between the float and the member 30 when water in the gas chamber 2 causes such closing.

In order to assemble the gas chamber 2, water compartment 3 and support 5 in an air and water tight manner, the gas chamber 2 has an annular flange 34 (FIG. 9), the support 5 has an annular flange 35, and the base 36 of the water compartment 3 has an extended flange 37 a part 38 of which is rolled over flanges 34 and 35 and a gasket 39 to provide the necessary water and air tight parts.

In use, the humidifier is connected between a source of supply of gases which are connected to the inlet 32 and an outlet (not shown) is connected to breathing apparatus associated with a patient in, for example, an intensive care area of a hospital. A water supply is connected to the inlet 12 and such water supply preferably is provided in the well known bag which is mounted on a pole adjacent to the patient. The humidifier is mounted on a heating device of known type and when water in the compartment 3 is heated to a sufficient temperature, water vapor, but not liquid water, passes through the microporous wall 4 into the gas chamber 2 and thus humidifies the gas passing therethrough to the patient. However, under some circumstances, there may be a break or other condition under which the liquid water may pass through the microporous wall into the gas chamber so that the water level in the gas chamber exceeds a predetermined level. Any liquid water so entering will raise the float 25 causing the member 30 to press the flexible membrane 20 against the valve seat 15 thus closing off water supply into the water compartment. Thus, in a very simple yet effective manner a control valve is provided which obviates or minimizes the risk of the gas chamber becoming flooded and liquid water being passed on to the patient.

In some cases it may be desirable to omit the microporous wall 4 so that the water compartment is in effect simply a lower part of the gas chamber 2. Also, even using the microporous wall 4 it might be thought desirable to have an exit as well as an entry water control valve for the water compartment 3. In such circumstances a safety valve of the same construction as above described is desirable and one such construction is shown in FIG. 11. In that construction, one float arm 26 has a member 41 which contacts and moves a part 42 of flexible wall 49 to close against valve seat 43 leading from the water entry 12, i.e. substantially similarly to the valve arrangement above described except side by side of another float (not shown) on a further set of arms 44 and 45. The arm is extended to provide an actuating member 46 which contacts a thickened part 47 of the flexible wall 49 to in turn contact the orifice of an exit passageway 48 leading to the gas chamber thus providing a water exit valve. One of the floats or valve actuators, e.g. the float actuating the arms 44, 45 and actuating member 46 to operate the thickened part 47 is preferably set so that valve 50 at the water entry is closed before the exit valve 51 to enable an observer to see if the water flow is usually controlled by valve 50.

In such construction humidification occurs off the surface of the water compartment 3, aided if necessary by using a porous material of large surface area in the gas chamber 2 to increase the water evaporation rate.

We claim:

1. Apparatus for humidifying gases comprising:
 a gas chamber having an inlet and an outlet to enable gases to be passed through said chamber;
 a water compartment below and interconnected with said gas chamber;
 a microporous wall between and common to said gas chamber and water compartment, said microporous wall being permeable to water vapor but substantially impermeable to liquid water;
 at least one float in said gas chamber;
 a water inlet means;
 a water conduit leading from said inlet means to said water compartment; and
 at least one water control valve comprising a movable valve member connected to said at least one float for operation thereby and a valve seat on said water conduit between said water inlet means and compartment, so that when more than a predetermined amount of water enters said gas chamber from said water compartment, said at least one float is raised by said water and actuates said movable valve member relative to and into closing engagement with said valve seat to prevent further entry of water into said water compartment.

2. Apparatus as claimed in claim 1 wherein:
 said at least one float comprises two floats;
 a water outlet means is provided communicating with said water conduit; and
 a second water control valve is provided comprising a second movable valve member connected to the other of said two floats for operation thereby, and a second valve seat is provided on said water conduit between said water outlet and said conduit, so that said second valve member is moved relative to and into closing engagement with said second valve seat by said other float.

3. Apparatus as claimed in claim 1 wherein:
 said moveable valve member comprises a flexible valve member; and
 said at least one float is mounted on float actuable means so that when more than said predetermined amount of water enters said gas chamber said float is raised to cause part of said float actuable means to press said flexible valve member against said valve seat to close off water supply from said water inlet means to said water compartment.

4. Apparatus as claimed in claim 3 wherein:
 said water inlet means comprises a water conduit mounting member provided with areas of substantial plastics material; and
 said valve seat comprises an annular protruding lip on said conduit mounting member surrounded by a depression provided an annular line contact with said flexible valve member when said control valve is closed.

5. Apparatus as claimed in claim 3 wherein:
 said flexible valve member is comprised of synthetic rubber material molded as part of said water conduit to form a part of a wall of said water conduit.

6. Apparatus as claimed in claim 3 wherein:
 a microporous wall support means is provided for resisting water pressure in said water compartment on said microporous wall;

a pair of flexible upstanding strips are provided on said support means; and said float actuable means comprise an arm means connected to said float, and slots in said arm means mounted on said flexible strips so that said straps bend when said at least one float is raised to provide for hinging movement of said float.

7. Apparatus as claimed in claim 1 and further comprising:

a support means for said microporous wall for resisting water pressure in said water compartment applied to said microporous wall.

8. Apparatus as claimed in claim 7 wherein:

said support means for said microporous wall comprises reinforcing ribs arranged in a pattern in a substantially horizontal plane, said ribs supporting areas of said microporous wall.

9. Apparatus as claimed in claim 7 wherein:

said water conduit comprises a part of said support means for said microporous wall.

10. Apparatus as claimed in claim 7 wherein:

said gas chamber comprises a bell shaped member having a lower peripheral portion and an outwardly extending annular flange surrounding said lower peripheral portion;

said support means for said microporous wall has a coacting annular flange portion; and said water compartment comprises a dish member having a coacting annular flange portion with an outer part rolled over said bell shaped member annular flange and said support means annular flange, said rolled over part compressing said flanges together to provide air tight and water tight joints between said gas chamber and said water compartment.

11. Apparatus for humidifying gases comprising:

a bell shaped member forming a gas chamber therein;

an inlet and an outlet in said bell shaped member to enable gases to be passed through said gas chamber;

a dish shaped member forming a water compartment interconnected with and below said gas chamber;

a microporous wall between and common to said gas chamber and water compartment, said microporous wall being permeable to water vapor but substantially impermeable to liquid water;

water conduit means passing through a part of said gas chamber;

support means for said microporous wall for resisting water pressure in said water compartment applied to said microporous wall;

a lower periphery on said bell shaped member;

an outwardly extending annular flange on and surrounding said lower periphery;

a coacting annular flange on said support means for said microporous wall; and a coacting annular flange on said dish shaped member having an outer port rolled over said annular flanges on said support means and said bell shaped member, said rolled over outer part compressing said flanges together to provide air tight and water tight joints between said gas chamber and said water compartment.

* * * * *